United States Patent [19]
Cook

[11] Patent Number: 6,071,918
[45] Date of Patent: Jun. 6, 2000

[54] COMBINATION OF AN OPIOID ANTAGONIST AND A SELECTIVE SEROTONIN REUPTAKE INHIBITOR FOR TREATMENT OF ALCOHOLISM AND ALCOHOL DEPENDENCE

[75] Inventor: Leonard Cook, Newark, Del.

[73] Assignee: Dupont Pharmaceuticals Company, Wilmington, Del.

[21] Appl. No.: 09/357,748

[22] Filed: Jul. 21, 1999

[51] Int. Cl.$^7$ .................. A61K 31/495; A61K 31/44; A61K 31/445; A61K 31/40; A61K 31/135

[52] U.S. Cl. ................ 514/253; 514/282; 514/321; 514/410; 514/649; 514/651; 514/657

[58] Field of Search .................... 514/282, 253, 514/321, 410, 649, 651, 657

[56] References Cited

U.S. PATENT DOCUMENTS 5,817,665  10/1998  Dante ........................... 514/282

OTHER PUBLICATIONS

D. R. Brown & S. G. Holtzman, Pharmacol. Biochem. Behav., 1979 11:567–573.

L. D. Reid & G. A. Hunter, Alcohol, 1984, 1:33.

C. L. Hubbell et al., Alcohol, 1986, 3:39.

R. D. Myers et al., Alcohol, 1986, 3:383.

C. L. Hubbell et al., Alcohol, 1991, 8:355.

D. V. Gauvin et al., Alcohol, 1993, 10:37.

C. A. Narango et al., Clin. Pharm. Ther., 1984, 35:374.

C. A. Narango et al., Clin. Pharm. Ther., 1987, 41:266.

T. W. Rall, in: Goodman and Gilman's The Pharmacological Basis of Therapeutics, A. G. Gilman et al. 8$^{th}$ Edition, Chap. 17, 378–379.

*Primary Examiner*—Raymond Henley, III
*Attorney, Agent, or Firm*—Karen H. Kondrad

[57] ABSTRACT

The invention relates to a method of treating alcoholism and alcohol dependence in a mammal comprising administering to the mammal a therapeutically effective amount of a synergistic combination of: (i) at least one opioid antagonist, and (ii) at least one selective serotonin reuptake inhibitor. The invention also relates to compositions and kits containing the same.

7 Claims, No Drawings

COMBINATION OF AN OPIOID ANTAGONIST AND A SELECTIVE SEROTONIN REUPTAKE INHIBITOR FOR TREATMENT OF ALCOHOLISM AND ALCOHOL DEPENDENCE

FIELD OF THE INVENTION

This invention relates to a method of treating alcoholism and alcohol dependence in a mammal comprising administering to the mammal a therapeutically effective amount of a synergistic combination of: (i) at least one opioid antagonist, and (ii) at least one selective serotonin reuptake inhibitor. This invention also relates to compositions and kits containing the same.

BACKGROUND OF THE INVENTION

The present invention is based on the theory that an unexpected and surprising synergy will be found with a combination therapy involving opioid antagonists and selective serotonin reuptake inhibitors which has been neither disclosed nor suggested by the prior art. Such a therapy would provide a new and highly beneficial method for the treatment of alcohol dependence.

Disulfiram (Antabuse®) and Naltrexone (Trexan®) are the only FDA approved products that are currently available for adjunctive use in the treatment of alcohol abuse (T. W. Rall, in: *Goodman and Gilman's The Pharmacological Basis of Therapeutics*, A. G. Gilman et al., 8th Edition, Chap. 17, pp. 378–379, Pergamon Press, 1990). Disulfiram works by blocking the intermediary metabolism of alcohol. Most alcohol is normally metabolized to acetaldehyde which is further oxidized to innocuous byproducts which are excreted or recycled through energy-producing or other biosynthetic pathways. When alcohol is consumed in the presence of disulfiram, blood acetaldehyde concentrations increase to many-fold higher than normal values and produce markedly adverse behavioral and physiological responses that are collectively described as the "acetaldehyde syndrome." Psychological theory suggests that patients will avoid further consumption of alcohol to avoid these alarming and potentially life-threatening responses.

Naltrexone blocks alcohol craving and reduces total alcohol consumption without producing mood changes or psychiatric symptoms. The applicant suggests that naltrexone may be particularly useful in preventing alcohol relapse. Naltrexone, a well-known narcotic antagonist, is thought to work by blocking activation of the endogenous opioid reward system. Hence, naltrexone blocks the action of endorphins, enkephalins, and other endogenous opioids which may be released in response to alcohol consumption. Similar results have been obtained in studies in rats and monkeys where naltrexone, naloxone, nalmefene, and other opioid antagonists have been shown to block the apparent rewarding effects of alcohol and reduce total alcohol consumption (D. R. Brown and S. G. Holtzman, *Pharmacol. Biochem. Behav.*, 11, 567, 1979; L. D. Reid and G. A. Hunter, *Alcohol*, 1, 33, 1984; C. L. Hubbell et al., *Alcohol*, 3, 39, 1986; R. D. Myers et al., *Alcohol*, 3, 383, 1986; C. L. Hubbell et al., *Alcohol*, 8, 355, 1991; D. V. Gauvin et al., *Alcohol*, 10, 37, 1993).

Medications that enhance brain serotonergic activity have also shown effectiveness in reducing alcohol consumption and are currently under evaluation for long-term treatment of alcoholism. For example, C. A. Naranjo et al., *Clin. Pharm. Ther.*, 35, 374, 1984, and *Clin. Pharm. Ther.*, 41, 266, 1987, have shown that the serotonin uptake inhibitors citalopram and zimeldine attenuate ethanol intake in non-depressed alcohol abusers. C. L. Hubbell et al., *Alcohol*, 8, 355, 1991, demonstrated that fluoxetine, another serotonin uptake inhibitor, attenuates alcohol intake in rats. In a review article, C. A. Naranjo et al., J. Clin. Psychiatry, 47, 16, 1986, indicate that several serotonin uptake inhibitors including zimelidine, citalopram, fluoxetine, and fluvoxamine decrease ethanol drinking in rats.

In the present invention, we claim an unexpected synergistic interaction between naltrexone, an opioid antagonist, and paroxetine, a serotonin uptake inhibitor, on alcohol fluid consumption in rats. The synergism may be demonstrated where small combined doses of naltrexone and paroxetine which are minimally active by themselves are more effective than maximally effective doses of either drug alone. Alternatively, the data may show that the observed median effective doses (ED50 responses) for various fixed dose combinations of naltrexone and paroxetine are significantly lower than can be accounted for by a simple additivity hypothesis. The data may show that the combination of a long-lasting opioid antagonist with a serotonin uptake inhibitor may provide a novel adjunctive treatment for alcohol abuse and alcoholism in man.

SUMMARY OF THE INVENTION

The present invention claims a method of treating alcoholism and alcohol dependence in a mammal comprising administering to the mammal a therapeutically effective amount of a synergistic combination of at least one opioid antagonist, such as naltrexone or nalmefene; and paroxetine. The present invention is also directed to compositions and pharmaceutical kits containing the same. Such combination therapy may provide surprisingly efficient and effective methodology for use in the treatment of alcoholism and alcohol dependence.

DETAILED DESCRIPTION OF THE INVENTION

The present invention provides a method of treating alcoholism and alcohol dependence in a mammal comprising administering to the mammal, in combination, a therapeutically effective amount of: (i) at least one opioid antagonist; and (ii) at least one selective serotonin reuptake inhibitor.

In the present invention, the applicant claims that the administration of an opioid antagonist (component (i)) in combination with a selective serotonin reuptake inhibitor (component (ii)) does result in an unexpected synergistic effect in the reduction of alcohol consumption. Thus, the reduction in alcohol consumption when an opioid antagonist is administered in combination with a selective serotonin reuptake inhibitor is greater than the additive effect of each agent when administered alone. This is a remarkable and unexpected effect in view of what is currently known in the literature. This synergistic combination is expected to greatly increase the efficacy of single agent or multiple agent treatments of alcoholism and alcohol dependence.

Thus, the present invention claims that an opioid antagonist may be administered in combination with a selective serotonin reuptake inhibitor, thereby reducing the doses of each drug required to achieve reduction in alcohol consumption. Moreover, the present invention claims that the use of the compounds of component (i) and component (ii) of the invention in combination results in a greater than additive effect. Thus, the combination treatment of the present invention of components (i), and (ii) permits the use of lower doses of each component, with reduced adverse, toxic effects of each component. It also provides for a greater window of efficacy, since the same maximum tolerated doses can be administered before toxic effects associated with each agent are observed. A lower dosage minimizes the potential of side effects of the compounds, thereby providing an increased margin of safety relative to the margin of safety for each component when used as a single agent.

As used herein, the term "opiate antagonist" refers to compounds or compositions which serve to block the action of endogenous or exogenous opioid compounds on narcotic receptors or narcotic receptor subtypes in the brain or periphery and include naltrexone (Trexan®), naloxone (Narcan®), nalmefene, naloxone methiodide, nalorphine, naloxonazine, naltrindole (NTI), naltrindole isothiocyanate, (NTII), naltriben (NTB), nor-binaltorphimine (nor-BNI), b-funaltrexamine (b-FNA), BNTX, cyprodime, ICI-174, 864, LY117413, and MR2266. Other compounds and compositions are known and will be readily apparent to those skilled in the art, once armed with the present disclosure. Such opioid antagonists may serve to block the positive reinforcing effect of ethanol which results from the release of endogenous opioids upon consumption of alcohol.

When terms narcotic antagonist or serotonin selective uptake inhibitor are used herein, it is to be understood that any of the pharmaceutically suitable salts thereof which have narcotic antagonist or serotonin uptake inhibiting properties in man and on other mammals are included by the term. Such salts include the hydrochlorides, hydrobromides, hydroiodides, sulfates, bisulfates, nitrates, citrates, tartrates, bitartrates, phosphates, malates, maleates, fumarates, succinates, acetates, terephthalates, and pamoates.

By "therapeutically effective amount" it is meant an amount of component (i), and component (ii) that when administered alone or in combination to a mammal is effective to treat alcoholism and alcohol dependence, such as by reduction of alcohol consumption and craving. Compositions of the invention present the opportunity of obtaining significant reductions in alcohol consumption with reduced dosages of the narcotic antagonist and serotonin selective uptake inhibitor components, thereby diminishing the side effects and possible toxicity which would result from the otherwise required amounts of the individual drug components.

By "administered in combination", or the like, when referring to component (i), and component (ii), of the present invention, it is meant that the components are administered concurrently to a mammal being treated. By concurrently, it is meant that each component may be administered at the same time or sequentially in any order at different points in time, however if not administered at the same time, they should be administered sufficiently closely in time so as to provide the desired treatment effect. Suitable dosing intervals and dosing order with such compounds will be readily apparent to those skilled in the art, once armed with the present disclosure. Preferably, all components are administered at the same time, and if not administered at the same time, preferably they are all administered less than one hour apart from one another.

In a composition of the invention, naltrexone and paroxetine are combined and will be utilized at various dose ratios based on weight of naltrexone and paroxetine in rats offered an opportunity to drink a sweetened ethanol solution or water. The ethanol drinking test [e.g., C. L. Hubbell et al., *Alcohol*, 3, 39, 1986] is a standard procedure for detecting and comparing the ability of different classes of compounds to increase or decrease alcohol consumption in rats and has a good correlation with the ability of compounds to modify human alcohol drinking. Data for the rat, as presented in a mixture model, can be translated to other species where the orally effective alcohol-modifying dose of the individual compounds is known or can be estimated. The method simply consists of reading the % effective dose for each dose ratio on the best fit regression analysis curve from the rat mixture model, multiplying each component by its effective species dose, and then forming the ratio of the amount of naltrexone to paroxetine. This basic correlation for antagonist properties enables estimation of the range of human effectiveness [E. W. Pelikan, *The Pharmacologist*, 1, 73 (1959)].

Application of an equieffective dose substitution model and a curvilinear regression analysis utilizing all the data for the individual compounds and various dose ratios for the combinations establishes the existence of unexpectedly enhanced alcohol drinking suppressing activity of combinations of naltrexone and paroxetine, i.e., the resulting activity is greater than the activity expected from the sum of the activities of the individual components.

The present invention also includes pharmaceutical compositions (that is, combination products), such pharmaceutical compositions (combination products) comprising, an opioid antagonist (such as naltrexone), and a selective serotonin reuptake inhibitor. Such compositions may be in solid, liquid, sustained release such as transdermal, transnasal, or depot dosage units and may further include a suitable pharmaceutical carrier.

The present invention also includes pharmaceutical kits comprising an opioid antagonist (such as naltrexone), together with a selective serotonin reuptake inhibitor. In the kit, the opioid antagonist and the selective serotonin reuptake inhibitor may each be presented in separate vials as compounds, and/or in separate vials as compounds in combination with a pharmaceutically acceptable carrier. Alternatively, the opioid antagonist and the selective serotonin reuptake inhibitor may be combined together in one or more vials, with or without a carrier. Thus, for example, the invention includes pharmaceutical kits comprising a separate vial comprising the opioid antagonist and a separate vial comprising the selective serotonin reuptake inhibitor, each vial also containing, if desired, a carrier.

The compositions and kits of the present invention may be employed in the treatment of alcoholism and alcohol dependence.

In the method of the present invention, the opioid antagonist (such as naltrexone) may be administered in combination with a selective serotonin reuptake inhibitor to achieve a synergistic decrease in alcohol consumption. Synergy occurs when the effect (such as reduction in alcohol consumption or craving) of the compounds when administered in combination is greater than the additive effect of the compounds when administered alone as a single agent. In general, a synergistic effect is most clearly demonstrated at suboptimal concentrations of the compounds.

The method of the present invention provides for an enhanced effect of the two drugs when administered in combination. Thus, the claimed combination treatment allows for the use of lowered clinical doses and increases the window of efficacy. In view of the marginal effects associated with the presently approved therapies for treating alcoholism and alcohol dependence, the present invention provides an important advantage over current therapies.

Opioid antagonists useful in the methods, compositions and pharmaceutical kits of the present invention include, but are not limited to naltrexone and nalmefene. These and other opioid antagonists will be readily apparent to those skilled in the art, once armed with the present disclosure.

The preparation of naltrexone is described in U.S. Pat. No. 3,332,950 (H. Blumberg et al.), the disclosure of which is hereby incorporated herein by reference in its entirety. Naltrexone is available commercially as "Trexan®", for which product information, including dosage and administration, is given in *Physicians' Desk Reference*, 47th Edition, 1993, pp 956–958. The preparation of nalmefene may be carried out using preparatory methods such as those described in J. Fishman, U.S. Pat. No. 3,814,768; E. F. Huhn et. al., J. Med. Chem. 18, 259 (1975); P. C. Meltzer et al., European Patent Application No. 140,367 and U.S. Pat. No. 4,535,157.

The preparation of paroxetine may be carried out in a number of different fashions, as will be evident to the skilled artisan. Such preparatory methods include, for example, those described in Malloy et al. GE Patent 2,500,110 and U.S. Pat. No. 4,314,081, the disclosures of each of which are hereby incorporated herein by reference in their entirety. Paroxetine is available commercially as "PAXIL®", for which the product information, including dosage and administration, is given in *Physicians' Desk Reference*, 52nd Edition, 1998, pp. 2851–2858.

The present invention claims that therapeutic agents of component (i), and component (ii) described above, when administered in combination, exert a synergistic effect, particularly, reducing the consumption of alcohol. Such combination treatment may allow the use of lowered clinical doses with increase efficacy and a wider safety window.

Component (i) of the present invention may also be provided as a pharmaceutical composition comprising a therapeutically effective amount of an opioid antagonist and a pharmaceutically acceptable carrier. Component (ii) of the present invention may likewise be presented as a pharmaceutical composition comprising a therapeutically effective amount of a selective serotonin reuptake inhibitor and a pharmaceutically acceptable carrier. Mixtures of the components (i), and (ii) with or without a pharmaceutically acceptable carrier, are also within the ambit of the present invention.

Dosage and Formulation

The opioid antagonist (component (i)), and selective serotonin reuptake inhibitor (component (ii)) combination treatment of the invention can be administered by any conventional means available for the use in conjunction with pharmaceuticals, either as individual separate dosage units administered simultaneously or concurrently, or in a physical combination of each component therapeutic agent in a single or combined dosage unit. The active agents can be administered alone, but are generally administered with a pharmaceutical carrier selected on the basis of the chosen route of administration and standard pharmaceutical practice.

The dosage administered will, of course vary depending on the use and known factors such as the pharmacodynamic characteristics of the particular agent, and its mode and route of administration; age, health, and weight of the recipient; nature and extent of symptoms, kind of concurrent treatment, frequency of treatment, and the effect desired. The recipient may be any type of mammal, but is preferably a human.

For use in the treatment of diseases characterized by abnormally high consumption of alcohol, by way of general guidance, a daily oral dosage of active ingredient(s) can be about 0.001 to 1000 mg/kg of body weight. Ordinarily a dose of 0.1 to 500 mg/kg per day in divided doses one to four times a day or in sustained release form is effective to obtain the desired results.

The compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in a mixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be a coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (compositions) suitable for administration contain about 1 milligram to 100 milligrams of active ingredient per unit. In these pharmaceutical compositions, the active ingredient will ordinarily be present in an amount of about 0.5–95% by weight based on the total weight of the composition.

The active ingredient may be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers and methods of preparing pharmaceutical dosage forms are described in *Remington's Pharmaceutical Sciences*, Mack Publishing Company, a standard reference text in this field.

Useful pharmaceutical compositions (dosage forms) for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredients in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets can be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Suspension

An aqueous suspension can be prepared for oral administration so that each 5 ml contains 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Each therapeutic agent component of this invention can independently be in any dosage form, such as those described above, and can also be administered in various ways, as described above. The component (i), and (ii) of the invention may be formulated together, in a single dosage unit (that is, combined together in one capsule, tablet, powder, or liquid, etc.) as a composition (combination product). When component (i), and (ii) are not formulated together in a single dosage unit, the opioid antagonist component (i) may be administered at the same time as the selective serotonin reuptake inhibitor component (ii) or in any order. For example, component (i) of this invention may be administered first, followed by administration of component (ii), or they may be administered in the reverse order. When not administered at the same time, preferably the administration of component (i) and component (ii) of this invention occurs less than about one hour apart. Preferably, the route of administration of component (i) and component (ii), of the invention is oral. The terms oral agent, oral release enhancer, oral compound, or the like, as used herein, denote compounds which may be orally administered. Although it is preferable that component (i), and (ii), of the invention are both administered by the same route (that is, for example, both orally) or in the same dosage form (that is, for example, as a tablet), the invention contemplates that they may each be administered by different routes (that is, for example, one component of the combination product may be administered orally, and another component may be administered intravenously) or in different dosage forms (that is, for example, one component as a tablet and another as a liquid).

As will be appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of component (i), and component (ii) in this invention will be readily ascertainable by a medical practitioner skilled in the art, based upon the present disclosure. By way of general guidance, typically a daily dosage may be about 10 milligrams to about 1.5 grams of each component. By way of general guidance, when the compounds of component (i) and component (ii) are administered in combination, the dosage amount of each component may be reduced by about 70–80% relative to the usual dosage of the component when it is administered alone as a single agent for the treatment of alcoholism and alcohol dependence, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one or more of the active ingredients may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one or more of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one or more components is coated with a sustained and/or enteric release polymer, and the other(s) component is also coated with a polymer such as a low viscosity grade of hydroxypropyl methylcellulose or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredients are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of alcoholism and alcohol dependence, which comprise a therapeutically effective amount of a compound of component (i), and a compound of component (ii), in one or more containers, are also within the ambit of the present invention. Sterilization of the container may be carried out using conventional sterilization methodology well known to those skilled in the art. Component (i), and component (ii) may be in the same container or in separate containers. The containers of materials may comprise separate containers, or one or more multi-part containers, as desired. Component (i), and component (ii), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

EXAMPLES

The examples described below may be used to demonstrate the synergistic effect of an opioid antagonist, such as naltrexone, administered in combination with a selective serotonin reuptake inhibitor. The tests described below may demonstrate that a representative opioid antagonist, naltrexone, acts synergistically with a representative selective serotonin reuptake inhibitor, paroxetine, resulting in reduction of total alcohol consumption in a model of sustained ethanol drinking behavior in rats.

Protocol

The methods for testing individual compounds for their ability to modify alcohol intake are essentially the same as described by C. L. Hubbell et al. in *Alcohol*, 3, 39 (1986). Male Sprague-Dawley rats are obtained from Charles River Breeding Laboratories. For 14–30 days, rats are given a 2 hour daily opportunity to drink a sweetened 10–20% ethanol solution or water. Rats are deprived of water for the remaining 22 hours each day. Rats eventually drink considerable amounts of ethanol solutions equivalent to about 1.0 to 3.0 g/kg of pure ethanol equivalent each day. After stable levels of alcohol intakes are achieved, various pharmacological preparations are tested for their effects on the intake of sweetened alcohol solutions. For the next few days, designated groups of rats are administered various oral doses of naltrexone, paroxetine, fixed-dose combinations of naltrexone and paroxetine, or water (vehicle) 10–30 minutes before their opportunity to drink ethanol solutions. In similar experiments, data may also be obtained using rats prepared by the "Samson" sucrose-fading procedure (D. V. Gauvin et al., *Alcohol*, 10, 37, 1993). In this procedure, rats are offered a 30 minute opportunity to drink sweetened ethanol solutions each day and are not water deprived for the remaining period each day. To induce a stable level of alcohol consumption, the concentration ratios of the sucrose-ethanol solutions are varied over days by increasing the ethanol concentration from 5% to 20% w/v and reducing, eventually to zero, the sucrose concentration. On day 1 only, rats are deprived of water for 16 hours prior to the introduction of 20% sucrose solutions. Thereafter, access to food and water is ad libitum except during the 30 minute ethanol-sucrose access test period each day. Rats are eventually maintained on 10% ethanol solutions during the daily test period. Test compounds are administered as described above.

All rats are dosed sequentially by the oral route with solutions or suspensions of naltrexone HCl and/or of paroxetine HCl. A dosing volume of 1 to 10 ml/kg is used for each sequential solution or suspension. All doses are coded and the test is performed under a code not known to the observer.

METHOD

The present study compared the effectiveness of naltrexone, a nonspecific opioid receptor antagonist, and paroxetine, a serotonin reuptake inhibitor in suppressing alcohol intake when administered alone and in combination. Adult male rats of the in-bred alcohol-preferring P-line were given 24-hour access to food and water and scheduled access to a 10% (v/v) alcohol solution for 2 hours daily. Naltrexone (2.0, 5.0, 10.0 or 20.0 mg/kg BW) and paroxetine (1.5, 3.0, 5.0, 10.0 or 20.0 mg/kg BW) were infused intragastrically alone or in combination 30 minutes prior to the 2-hour alcohol access period.

The hypothesis that the effects of naltrexone and paroxetine on suppression of alcohol consumption are additive was tested using a Mixture Model (Cornell, J. A., Experiments with Mixtures: Designs, Models, and the Analysis of Mixture Data $2^{nd}$ Edition, Wiley-Interscience, New York, 1990). In this model the suppression of alcohol consumption is assumed to be dependent on the proportions of the components of the mixture and on the total amount of treatment. In this case, we have a two (2) component mixture where each component presents a linear, dose dependant suppression of alcohol consumption. The proportions of each component of the mixture are varied in such a way that the total amount of treatment is constant at 20 mg/kg and the total suppression of alcohol consumption becomes dependent on the proportions of the components in the mixture. The null hypothesis is that the effects of the two (2) components combined are additive and that the result of treatment with the mixture will be equivalent to the maximum effect of either drug alone. Significant deviation from that maximum will disprove the additivity hypothesis and be indicative of an unexpected synergistic effect of the combined treatments.

RESULTS

Naltrexone alone at doses of 10.0 and 20.0 mg/kg and paroxetine at 3.0, 5.0, 10.0 and 20.0 mg/kg p.o. significantly suppressed alcohol consumption in a dose dependent manner (FIG. 1). The maximum suppression for both drugs was approximately 55%.

suppression of alcohol consumption using the combination. There is no significant effect of the combination treatment on water consumption (FIG. 3), indicating that the greater than expected suppression of alcohol consumption is selective for alcohol. The data then disproves the null hypothesis and indicates that the combined treatment gives a greater than expected suppression of alcohol consumption and is synergistic.

Naltrexone when administered alone evidenced a short duration of action (<24 h) whereas the effect of paroxetine when administered alone was more prolonged (24–48 h). The duration of action of naltrexone/paroxetine combination was also 24–48 h.

CONCLUSIONS

Given that naltrexone and paroxetine are orally active, have few side effects, act synergistically to reduce alcohol intake and evidence a prolonged duration of action, this drug combination may be therapeutically useful in the treatment of alcohol dependence.

FIG. 1: Both naltrexone and paroxetine suppress alcohol consumption in in-bred alcohol preferring (P-line) rats. The effect is dose dependent and linear. *: P<0.05 from control, ANOVA and Fisher's PLSD. †: significant decrease in water consumption, p<0.05 from control, ANOVA and Fisher's PLSD.

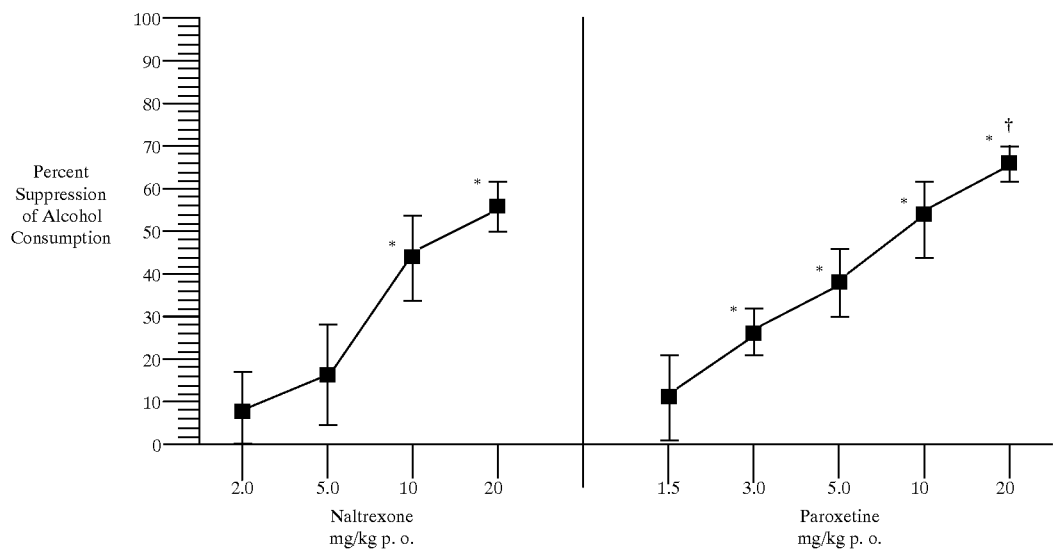

The effect of the combined treatment with naltrexone and paroxetine (FIG. 2) significantly (p=0.004) deviates from the expected additive nature of the mixture. All mixtures of naltrexone and paroxetine suppressed alcohol consumption (76–90%) to a greater degree than maximum suppression of either drug alone. This indicates a greater than expected FIG. 2: Using a Mixture Model, the combination of naltrexone and paroxetine produces an unexpectedly large suppression of alcohol consumption in in-bred alcohol preferring (P-line) rats. The observed level of suppression is significantly greater (p<0.004 by ANOVA) than the expected level and is considered synergistic.

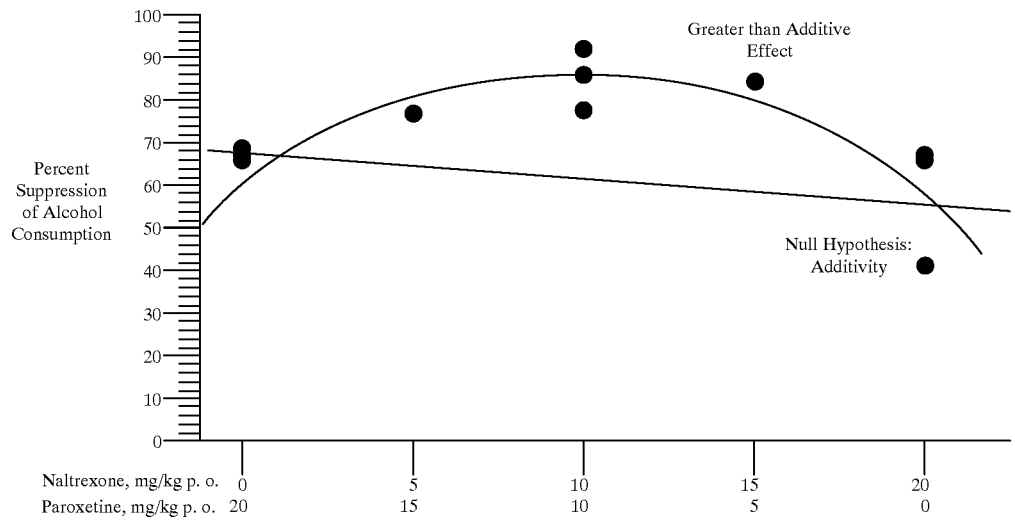

FIG. 3: Neither naltrexone nor paroxetine alone or the combination alters water consumption in a Mixture Model using in-bred alcohol preferring (P-line) rats. The water consumption values for the mixture do not significantly differ from the expected values. The values shown are the mean and SEM for all the animals tested in the experiments shown in FIG. 2.

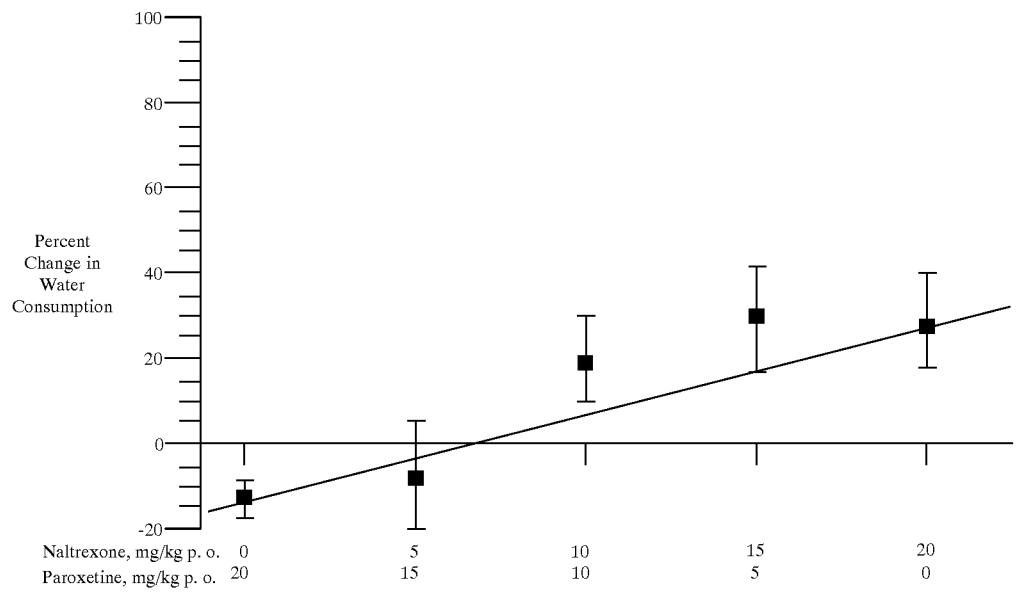

What is claimed is:

1. A method of treating alcoholism and alcohol dependence comprising administering to a mammal a therapeutically effective amount of a synergistic combination of: (i) at least one opioid antagonist; and (ii) at least one selective serotonin reuptake inhibitor paroxetine.

2. A method of claim 1 wherein said opioid antagonist is naltrexone and wherein said selective serotonin reuptake inhibitor is paroxetine.

3. A method of claim 1 or 2 wherein said mammal is a human.

4. A method of claim 1 or 2 wherein said administration is oral.

5. A pharmaceutical composition comprising a therapeutically effective amount of a synergistic combination of at least one opioid antagonist and paroxetine.

6. A composition of claim 5 wherein said opioid antagonist is selected from the group consisting of naltrexone, nalmefene, and naloxone and wherein said selective serotonin reuptake inhibitor is paroxetine.

7. A composition of claim 6 wherein said opioid antagonist is naltrexone and wherein said selective serotonin reuptake inhibitor is paroxetine.

* * * * *